United States Patent
Kaplan et al.

[19]

[11] Patent Number: 5,956,144
[45] Date of Patent: Sep. 21, 1999

[54] METHOD AND APPARATUS FOR USE OF POLARIZED LIGHT VECTORS IN IDENTIFYING AND EVALUATING CONSTITUENT COMPOUNDS IN A SPECIMEN

[75] Inventors: Milton R. Kaplan, San Antonio; John Cernosek, West, both of Tex.

[73] Assignee: Micro Research, Inc., San Antonio, Tex.

[21] Appl. No.: 08/392,728

[22] Filed: Nov. 22, 1995

Related U.S. Application Data

[63] Continuation-in-part of application No. PCT/US93/08319, Sep. 3, 1993, and application No. 07/940,075, Sep. 3, 1992, abandoned.

[51] Int. Cl.[6] ....................................................... G01J 4/00
[52] U.S. Cl. ........................ 356/364; 356/368; 128/633; 128/665
[58] Field of Search .................................... 356/364–369, 356/41, 319, 322, 326, 327; 128/633, 635, 634, 664–666

[56] References Cited

U.S. PATENT DOCUMENTS

| | | | |
|---|---|---|---|
| 3,724,952 | 4/1973 | Vossberg | 356/368 |
| 4,011,014 | 3/1977 | Tanton | 356/367 |
| 4,901,728 | 2/1990 | Hutchinson | 356/368 |
| 5,009,230 | 4/1991 | Hutchinson | 356/368 |
| 5,209,231 | 5/1993 | Cote et al. | 356/368 |

FOREIGN PATENT DOCUMENTS

| | | | |
|---|---|---|---|
| 4043659 | 2/1992 | Japan | 356/369 |

*Primary Examiner*—Hoa Q. Pham
*Attorney, Agent, or Firm*—David G. Henry

[57] ABSTRACT

A device and method for determining the identity and concentration of constituent compounds of a test specimen. The device and method are based upon the polarization effect that a specimen will have when subjected to randomly polarized light. This polarization effect will cause the intensity of light wither reflecting from or passing through the test specimen at one angle of polarization to be different then the intensity of light exiting the specimen at a second angle of polarization at a specific wavelength. The intensity of light either reflecting from or exiting the test specimen various planes of polarization is accurately measured by irradiating the specimen with randomly polarized light and then polarizing the light reflected from or passing through the specimen in different planes of polarization angles and measuring the intensity of light in each of these polarization planes at one or more wavelengths of light. These measurements will yield a unique pattern determined by the ratio of intensity of light either reflected or passing through the specimen per degree of polarization per wavelength.

6 Claims, 5 Drawing Sheets

Figure 4b $\Phi_o$ Degrees

Figure 5a

Figure 5b $\Phi_o + \delta_o$ Degrees

Figure 6a

Figure 6b $\Phi$ Degrees

Figure 7a

$\delta_o$   $\bar{\phi}+\delta_o$ Degrees

Figure 8b   $\bar{\phi}$ Degrees

Figure 9a

Figure 9b   $\bar{\phi}+\delta_o$ Degrees

Figure 10

METHOD AND APPARATUS FOR USE OF POLARIZED LIGHT VECTORS IN IDENTIFYING AND EVALUATING CONSTITUENT COMPOUNDS IN A SPECIMEN

This is a continuation-in-part of U.S. application Ser. No. 07/940,075 filed Sep. 3, 1992 (03.09.1992) now abandoned and of PCT/U.S. 93/08319 filed Sept. 3, 1993.

BACKGROUND OF THE INVENTION

1. Field of The Invention

Applicant's invention relates to the field of polychromatic polarimetric analysis of test specimens to determine the identity and concentration of the constituent elements or compounds of the test specimen. The invention relates more specifically to an apparatus and method for utilizing spectral transmission signatures involving polarization analysis for known compounds to identify and quantify those compounds in unknown test specimens.

2. Background Information

Presently, there are several different methods employed for identifying constituent compounds in a test specimen and determining the concentration of each compound. Chemical analysis of a specimen is frequently undertaken and usually yields excellent results. However, certain specimens, including internal bodily fluids, are not well suited for chemical analysis, because they can only be chemically analyzed by undertaking an invasive procedure that may be painful and may risk infection. For this reason, an accurate, non-invasive analytical method is needed for determining the identity and the concentration of various contituent compounds, such as glucose, alcohol or narcotic substances, in internal bodily fluids, such as blood.

Among the most promising tools for performing a non-invasive analytical procedure is by using spectrophotometric analysis. Spectrophotometric analysis relies on the principle that every compound has a unique "pattern" determined by the amount of light absorbed (or transmitted or reflected) by the compound at different wavelengths. Typically, analytical spectro-photometric methods target the specimen with light of known intensity, and measure the absorption of light by the specimen, at various wavelengths, or conversely, measure the intensity of light passing through the specimen, at various wavelengths, and then compare this "pattern" of absorption (or intensity) at different wavelengths with the known pattern of absorption per wavelength of various compounds.

Unfortunately, typical spectrophotometric analysis of a specimen is only of limited usefulness when the specimen is complex, (i.e. contains several compounds or elements), or if the density of the specimen is unknown, because absorption of light (or intensity of transmitted light) may be directly affected by these variable factors. Thus, relying solely on the absorption of light at various wavelengths does not yield a sufficiently accurate non-invasive method for analysis of bodily fluids. Certainly, the detection and measurement of other optical factors, which are unique for each compound, in addition to measurement of the absorption of light by the specimen per wavelength, would greatly improve the efficiency and accuracy of any spectroscopic technique used for determining the identity and concentration of constituent elements in a specimen.

In an attempt to provide a more accurate test and overcome other limitations of conventional spectrophotometric analysis of a specimen, several procedures have been developed using polarimetric analysis. Polarimetric analysis uses polarized light rather than partially polarized polychromatic light to irradiate the specimen and relies on the principle that specimens containing an optically active compound, such as glucose, will rotate the plane of polarized light, thereby causing a measurable "shift" in the plane of polarization. The degree and direction of the polarization shift that is caused by a compound is unique for each compound. In addition, certain compounds "depolarize" polarized light in is a unique manner.

Thus, by irradiating a test specimen with light that is polarized in a predetermined plane and then measuring the polarization shift and/or the degree of depolarization of tie light caused by the constituent components of the specimen at various wavelengths, the identity of the components in a specimen, as well as the respective concentrations of the components, theoretically can be more readily determined than by measuring only the absorption of light at each measured wavelength. Examples of prior-issued patents which are known to Applicant, and which relate to the use of polarized light in performing a spectroscopic analysis of a specimen, include the following:

U.S. Pat. No. 3,724,952 issued to Vossberg on Apr. 3, 1973, describes an apparatus and method for polarimetric analysis of a specimen, comprising the use of light that is polarized in one plane prior to passage of the light through the specimen. After the polarized light passes through the specimen, it passes through an analyzer and detector, which determine the "polarization shift" caused by the components of the specimen, as well as the degree of depolarization and the absorption of light by the specimen.

U.S. Pat. No. 4,901,728 and U.S. Pat. No. 5,009,230 issued to Hutchinson on Feb. 20, 1990 and Apr. 23, 1991, respectively, describe a device for non-invasive determination of blood glucose of a patient, by passing two orthogonal and equally polarized states of infrared light of the same intensity through a specimen and then passing the light through a polarizer to determine the rotation of the polarized light caused by the glucose in the specimen. The polarization shift is measured by calculating the difference in intensity of the two states of polarized light exiting the polarizer.

U.S. Pat. No. 4,011,014 issued to Tanton on Mar. 8, 1977 describes a machine for testing the rotation of polarized light by translucent specimens, that includes a polarizer to polarize light prior to the light contacting the specimen, and then measuring the polarization shift and other optical factors, that are caused by the specimen.

Each of the above-described methods and apparatuses for polarimetric analysis relies exclusively upon the principle of irradiating the specimen with light that is already polarized in a predetermined plane, and then measuring the polarization shift or other variables caused by the rotation of the polarized light by optically active compounds in the specimen. Although using polarized light to measure the "polarization" shift and/or other data dependent on the rotation of polarized light by the specimen, does provide certain information that can be objectively measured, in addition to the factors presented by standard spectrophotometric analysis, the use of light that already is polarized to irradiate the specimen has severe drawbacks.

For example, polarizing the light prior to irradiating the specimen significantly decreases the amount of light actually reaching the specimen, because a percentage of the light will be reflected or absorbed by the polarizing means before the light reaches the specimen. Obviously, when the specimen is dense, this loss of light could dramatically impact the amount of light actually passing through the specimen and capable of being measured.

In addition, polarizing the light in a particular plane of polarization before the light reaches the specimen, effectively eliminates all other planes of polarization in which the light travels, thereby drastically reducing the potential data that could be gathered if the light targeted on the specimen was randomly polarized light. In essence, trying to identify a compound in a complex specimen, by considering only the optical factors of light traveling through the specimen in a single plane of polarization is analogous to trying to formulate an accurate voter opinion poll by considering the opinion of only one or two persons. Obviously, the more voters that are considered, the more accurate will be the poll.

The inadequacy of the limited information obtained by using polarized light to irradiate a specimen is especially evident when the specimen contains two or more compounds, because the compounds may cause similar polarization shifts in the specific polarization plane in which the light is polarized, thereby making it very difficult to determine the identity and concentration of the different compounds in the specimen. The presence of more than one compound in the specimen may also "mask" the polarization shift that is actually caused by the targeted compound sought to be identified, because the presence of other compounds in the specimen may cause an enhancement or decrease in the polarization shift at the specific polarization plane in which the light is polarized. This masking effect on the polarization shift may cause either the identity or the concentration of the targeted compound to be incorrectly determined.

Measuring the polarization "shift" of light also requires that a polarizer be physically placed upstream from the specimen, to polarize the light in a specific plane of polarization prior to irradiating the specimen, and a separate polarizer/analyzer be physically placed downstream of the specimen through which light exiting the specimen is passed. This required use of two polarizers clearly causes the device to be more cumbersome and expensive than an invention that only requires the use of one polarizer.

Additionally, practicing certain inventions, such as the inventions disclosed in the Hutchinson patents, that use two beams of polarized light to measure the polarization shift and other factors related to rotation of the polarized light caused by optically active elements in the specimen, complicates matters considerably, because dual mechanisms are necessary to control the optical variables for each beam, such as the intensity of light and angle of polarization.

As briefly shown by the foregoing, both conventional spectrophotometric analysis and polarimetric analysis of a test specimen are severely hampered by the limited amount of data that can be obtained by merely measuring the absorption of light per wavelength by the specimen or by using polarized light to irradiate the specimen. Clearly, a method and apparatus is needed that would identify and accurately measure a wider range of optical factors than is possible by using standard spectrophotometric analysis or polarimetric analysis.

A starting point to the solution of the problem lies in the well developed electro-optical probe technologies currently in use in university, industrial, and government laboratories. The sensitivity of such probes may be increased enormously by taking advantage of the wavelength dependence of the polarized light. All wavelength components of polychromatic light are polarized, but not in the same way, and each must be examined separately. Each wavelength responds differently to a specific optically active medium.

After adding the analysis of wavelength it is advantageous to add the more complex analysis of the polarization rotational characteristics that result from the irradiation of many substances, especially organic. In general, organic molecules are structured in spiraled form and have a definite helicity or handedness. It is this helicity which gives a molecule its ability to rotate the polarization of the incident light. For example, dextrose (d-glucose) is, by convention, right-handed since, when viewed from the perspective of light emerging from the sample, the polarization axis has rotated in a clockwise direction. On the other hand, levulose (fruit sugar) is left-handed since it rotates the polarization axis in a counter clockwise direction. Molecules or material which exhibit this kind of optical activity are said to possess optical rotary power. In particular, these are termed dextrorotary or levorotatory respectively depending upon the action on the polarization of the incident light. The magnitude of the angle, through which the polarization direction rotates is, in simple theory, proportional to the inverse of the wavelength of the incident light squared. Sometimes called a dispersion function, this relationship has a weak dependence on wavelength but is strongly a function of the type of material or molecular structure being irradiated. This functional dependence on the physical properties of the sodium manifests itself in the difference of the indices of refraction for right- and left-handed polarized light. Two circularly polarized waves of opposite helicity form a set of basic fields for the description of any general state of polarization. As a result, for example, if the polarization of the light irradiating the sample were purely elliptical not only would the ellipse rotate by about an axis parallel to the direction of propagation of the light, but the ellipse also distorts—its eccentricity changes. This latter phenomenon is called circular dichroism. It is due to the different absorption between right- and left-handed circularly polarized light.

In a fluid, where there is no long-range order, the molecules are randomly oriented. Nevertheless, the effect of rotary power is not averaged out to zero. Since the constituent molecules all have a definite helicity which is the same, they cannot be brought into coincidence with their mirror images—they are enantiomorhpous. Thus, the effect of the rotary power of an individual molecule is enhanced in a fluid state. Substances which exhibit both optical rotary power and circular dichroism are referred to as chiral media.

A glucose solution is an isotropic chiral substance. When plane-polarized light impinges normally on glucose the vibration ellipse of the transmitted light is different from the vibration ellipse of the incident light. The difference is characterized by two quantities: (i) Optical rotation (OR), which is the angle by which the transmission ellipse rotates with respect to the incidence ellipse; (ii) Circular dichroism (CD), which is a measure of the difference in the eccentricities of the two ellipses. Profiles of the OR and the CD of an isotropic chiral substance with respect to frequency are sufficiently unique that they can be used as a component in the signature of a substance to be identified. Because the OR and the CD of any substance have been shown to be Kramers-Kronig-consistent, complete knowledge of either of the two quantities as a function of the frequency is sufficient to determine the other; therefore, the more easily measured OR is often used to characterize isotropic chiral substances.

A first issue that must be addressed is that of polarization of the light incident on the biological sample whose glucose content has to be monitored. Let us suppose that the incident light is a planewave traveling in the +z direction (of a cartesian coordinate system) at a frequency f. The electric field phasor associated with this planewave may be adequately set up as $$E_{inc}(z,t)=[A_x u_x + A_y u_y]e^{-i2\pi f(t-z/c_0)}, \quad (1)$$

where t is time and $c_0=3\times10^8$ m/s is the speed of light in free space; $i=\sqrt{(-1)}$; $(u_x, u_y, u_z)$ are the unit cartesian vectors; and $A_x$ and $A_y$ are complex amplitudes with units of V/m.

Let the complex amplitudes be independent of time t. In general, Eq. (1) then represents an elliptically polarized planewave whose vibration ellipse does not change with time t. When either $A_x=0$ or $A_y=0$, the planewave is said to be linearly polarized. When $A_x=\pm iA_y$, the planewave is circularly polarized.

Suppose now that $A_x$ and $A_y$ are functions of time t. Then Eq. (1) should be rewritten as $$E_{inc}(z,t)=[A_x(t)u_x + A_y(t)u_y]e^{-i2\pi f(t-z/c_0)}. \quad (2)$$

It still denotes a planewave, but one whose vibration ellipse changes with time t. Complicated sources have to be utilized in order to deliver specific $A_x(t)$ and $A_y(t)$. Indeed, the prior art devices utilize a complicated light source that yields $A_x(t)$ and $A_y(t)$ as controllable functions of time t.

The preferred embodiment of the present invention, however, utilizes a source based on Quartz-Tungsten-Halogen (QTH) lamp whose output in the focal region is partially polarized. Other suitable light sources include devices which emit light at multiple frequencies, such as LEDs. To understand the term "partially polarized", it is best to begin by thinking about "totally unpolarized" planewaves. The functions $A_x(t)$ and $A_y(t)$ are continuously random functions of time for a totally unpolarized planewave, therefore the rotation of a totally unpolarized planewave by a glucose cell cannot be measured and even the concept is of no meaning.

A partially polarized planewave can be thought of as a combination of a totally unpolarized planewave and an elliptically polarized planewave. The second component of the partially polarized wave suffers a definite rotation on passage through a glucose cell, therefore can be used for OR measurements.

The present invention has a source that delivers a slightly polarized planewave, thus its rotation by the glucose cell is meaningful.

A second issue that must be addressed is that of chromaticity. The devices described in the prior art ideally need monochromatic sources, i.e., sources whose outputs are fixed at precisely one frequency. Practical monochromatic sources cannot be ideal, instead their frequency range is very small.

Suppose $f_c$ is the center-frequency of a source and its 3-db bandwidth in denoted by $\Delta f$; then, we can define a quality factor $$Q=f_c/\Delta f. \quad (3)$$

The QTH lamp used in the preferred eabodiment of the present invention is a white-light lamp operating from 400 to 2000 nm with a peak at 900 nm; thus, its useful frequency spectrum ranges from $1.5\times10^{14}$ Hz to $7.5\times10^{14}$ Hz with its peak intensity at $3.3\times10^{14}$ Hz. As the QTH output is roughly independent of the frequency over the operating range, we can estimate its Q=3.3/(7.5−1.5)=0.55. Thus, the QTH lamp is definitely a polychromatic source.

The present invention also utilizes a polarization-preserving analyzer whose response is flat over the $2.3\times10^{14}$ Hz to $4.3\times10^{14}$ Hz range, and it uses a compensated polychromatic detector to measure the intensity of the beam transmitted by the analyzer. In sum, the present invention is polychromatic (low-Q), while the devices described in the prior art are monochromatic (high-Q).

Polychromaticity has a definite advantage over monochromaticity for such things as blood glucose measurements. The OR spectrum of a chiral solute in a non-chiral solvent depends on the concentration of the solute. The amount of glucose in a (diabetic) biological sample varies with time. A polychromatic system therefore has a much better chance of monitoring a continuously varying non-normoglycemic sample than a monochromatic one.

SUMMARY OF THE INVENTION

It is an object of the present invention to provide an apparatus and method for accurately determining the identity and concentration of constituent compounds of a test specimen, by irradiating the specimen with partially polarized light and calculating the intensity of light passing through or reflected from the specimen at various degrees of polarization and at various wavelengths.

It is another object of the present invention to provide a novel apparatus and method for accurately determining the identity and concentration of compounds contained in a test specimen.

It is another object of the present invention to provide a non-invasive apparatus and method for accurately determining the identity and concentration of compounds contained in a test specimen.

It is a further object of the present invention to provide an apparatus and method for spectroscopic analysis of a specimen that is able to identify and accurately measure a wider range of optical factors than is possible by using standard spectrophotometric analysis or polarimetric analysis.

It is another object of the present invention to provide an apparatus and method that permit accurate, non-invasive detection and concentration measurement of substances carried in the inner bodily fluids of a test subject.

It is another object of the present invention to use partially polarized light in irradiating a test specimen in polychromatic polarimetric analysis, so as to maximize the emission of light from such specimen.

It is a further object of the present invention to provide a non-invasive apparatus and method which maximizes the emission of light from a test specimen undergoing spectroscopic analysis, so as to provide useful data concerning light emissions from the specimen at multiple planes of polarized light.

It is another object of the present invention to provide a non-invasive apparatus and method for accurately determining the identity and concentration of compounds contained in a test specimen, by using partially polarized light to irradiate the test specimen and determining the extent to which the partially polarized light is naturally polarized by the constituent components of the test specimen.

In satisfaction of these and related objectives, Applicant's present invention teaches a novel non-invasive method and apparatus for identifying compounds in a test specimen, such as blood, by irradiating the test specimen with partially polarized light and then measuring the intensity of light passing through or reflected from the specimen at various degrees of polarization and at various wavelengths.

Unlike the methods and apparatuses used for standard spectrophotometric or polarimetric analysis, applicant's invention relies on the heretofore unrecognized principle that each element or compound has a recognizable and unique pattern determined by the intensity of light that it transmits or reflects at various angles of polarization and at various wavelengths. Thus, the identity and concentration of a compound can be accurately determined by determining the intensity of light passing through or reflected by the compound per degree (or smaller unit) of polarization per wavelength. Applicant's invention permits its practitioner to more accurately determine the constituent compounds of a specimen than is possible using conventional spectrophotometric analysis or by irradiating the specimen with polarized light.

BRIEF DESCRIPTION OF THE DRAWINGS

Applicant's invention may be further understood from a description of the accompanying drawings wherein, unless otherwise specified, like reference numbers are intended to depict like components in the various views.

DETAILED DESCRIPTION OF THE PREFERRED EMBODIMENT

Figure 1:
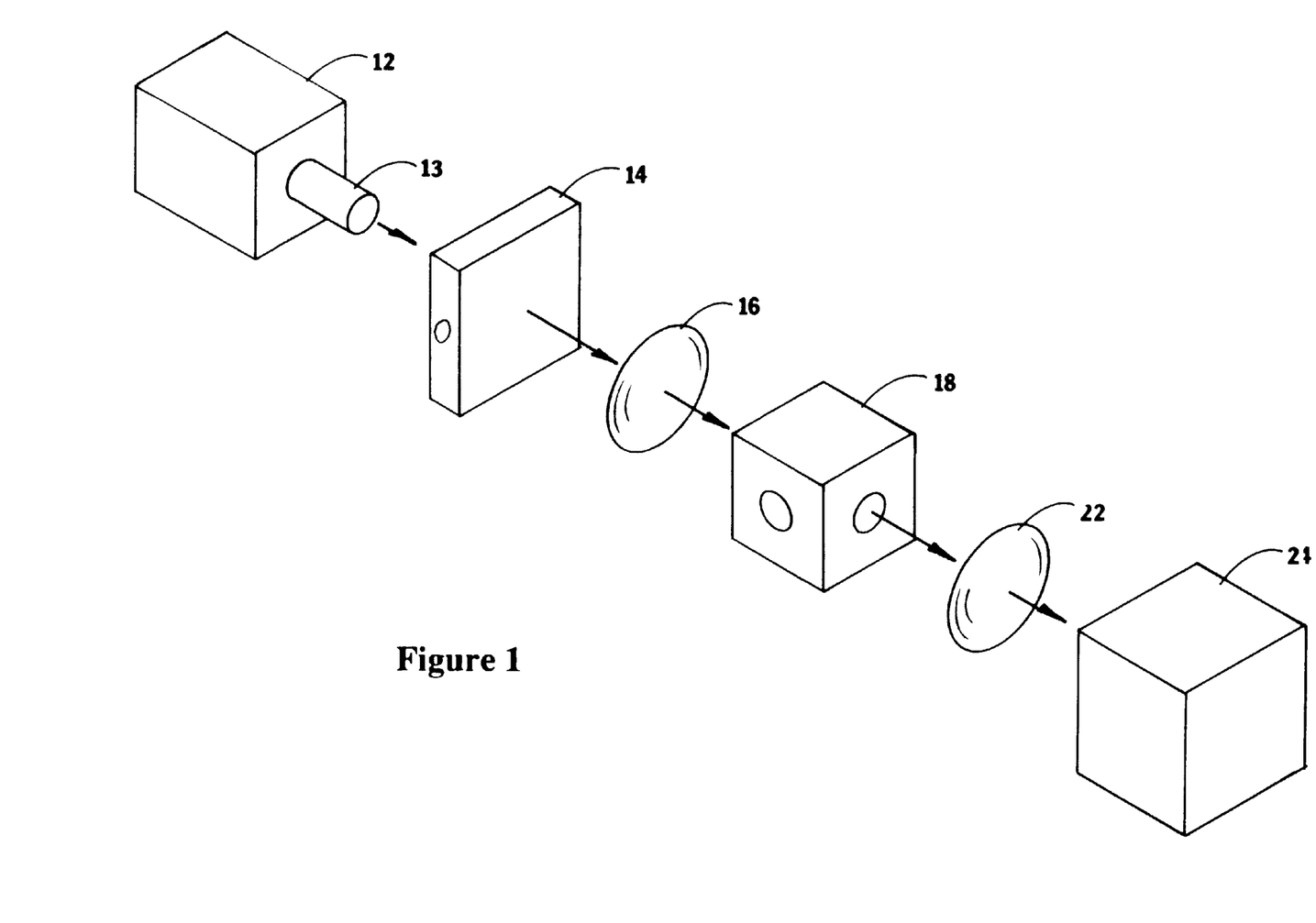
FIG. 1 is a perspective view of a preferred component composition of the optical path of Applicant's invention.

Referring to FIG. 1, utilization of Applicant's invention involves configuring an optical path (10). The preferred embodiment of Applicant's invention will involve the components of optical path (10) being incorporated into a small, hand-held unit (not shown in the drawings). Optical path (10) includes a light source (12). The light source (12) in the preferred embodiment of Applicant's invention is a tungsten halogen lamp, but the light source (12) may be any suitably energized radiation source that creates appropriate partially polarized polychromatic radiation. The peak radiance of the light source in the preferred embodiment, when directed towards the detection of glucose occurs at a value of approximately 900 nm. The spectral range of primary relevance for the glucose measurements is 800 nm–2000 nm, thus making this an ideal source. The emitted light of this source is partially polarized, but with a dominant elliptical character due to its internal elliptically contoured reflecting mirror. In addition, randomly or partially polarized radiation, limited to specific range(s) of wavelengths, can be utilized through use of a light source, such as a laser source, or by the use of a monochrometer. Such a modification would be advantageous in particular applications, when a narrow frequency band of light is desired (most likely because of the particular light transmission properties of the analyzed specimens).

For certain analytical purposes involving measurement of certain constituents, an optional element in the second position can be an optical filter housing (13). For use with the preferred embodiment, laser line filters are employed—separately—with spectral transmissions at 850 n.; 905 nm; and 1064 nm. This may provide supplemental information of possible interest in developing signatures for individual constituent elements.

The next item in the optical path (10) is a test specimen (14). The test specimen (14) may be a vial of blood or other bodily fluids or tissues or, in non-invasive tests, may be a patient's ear lobe, finger, wrist, etc. (not shown in the drawings). The sample is placed directly after the optical filter housing (13), if used, or any body part which can be suitably positioned for analysis using a device of Applicants' invention. For in-vitro testing, the sample solution is placed in a cuvett which in turn is mounted in a cuvette holder. Within the spectral region of concern, the cuvettes should produce literally no reflection and possess greater than 98% transmission.

For in-vivo testing, a preferred embodiment of the present invention utilizes a rectangular finger mount which should be highly reflective to background radiation and source generated noise. A circular aperture of diameter 6.50 mm through the full width of the mount is centered on the rectangular faces allowing for the entrance and exit of light. A cylindrical finger port perpendicular to and intersecting the aperture is positioned on one side of the mount. The design of the mount should be such that there will be a constant optical path length per individual for various measurements.

The constituent compounds of the test specimen (14) will naturally polarize and rotate the polarization of the beam of light passing therethrough, thereby causing the intensity value of light exiting from the test specimen (14) in a first plane of polarization to differ from the intensity value of light exiting from the test specimen (14) in a second plane of polarization and will effect a circular dichroism for the partially polarized light as described in FIGS. 6a–b, 7a–b, 8a–b, and 9a–b. Conversely, in the absence of a test specimen (14), the intensity value of light at a specific wavelength in each plane of polarization would be substantially identical and no circular dichroism would be seen.

The next component of the optical path in Applicant's preferred embodiment is a convex BK-7 lens (16) Lens (16) merely serves to focus the light originating from the light source (12) and transmitted through the test specimen (14) onto an adjustable polarizer or analyzer (18). Analyzer (18) polarizes the light as is transmitted through the test specimen (12) and emits the light along one or more specified polarization planes (20). The preferred embodiment of Applicant's invention includes a Glan Thompson polarizer as analyzer (18), because such a polarizer absorbs or reflects a relatively small portion of the light passing through it and can be easily adjusted between zero and 360 degrees of rotation to coincide with any polarization plane of light as exits the test specimen (14).

An acceptable substitute for a mechanical analyzer (18), such as the Glan Thompson polarizer would be an electromagnetic field capable of effecting polarization of the light as it exits the specimen (14), polarizing maintaining fiber optic or Glan Thompson analyzer.

A second convex BK-7 lens (22) is placed after the analyzer (18) to focus the light exiting the analyzer (18) onto a detector panel (24), such as an ORIEL silicon detector (available from ORIEL Corp.; 250 Long Beach Blvd; Stratford, Conn. 06497).

The detector (24) is linked to an analyzer (not shown in the drawings), such as a standard spectrophotometric analyzer or other means, to measure and analyze the intensity of the polarized light at multiple wavelengths. A preferred analyzer for this purpose is a lock-in amplifier device such as the Merlin Optical Radiation Measuring System (also available from ORIEL Corp).

In addition to the analyzer, an oscilloscope (not shown in the drawings) such as a Tech 2438 oscilloscope, may be linked to the detector (24) in the preferred embodiment of Applicant's invention, to allow a visual observation of the relative magnitude of the intensity of light being detected by the detector (24) in each of the analyzed polarization planes.

When the light source (12) is activated, the light travels the optical path and the intensity value of the light in a first plane of polarization is detected by the detector (24) and is measured at multiple wavelengths by the analyzer. After this first measurement, the analyzer (18) is rotated to change the plane of polarization of the light emitted from the analyzer (18) to a second polarization plane and the intensity value of the light in this second polarization plane is measured at multiple wavelengths. This process of rotating the analyzer (18) to distinguish and measure the intensity of light in each of several polarization planes, at one or more wavelengths, is continued until sufficient intensity values have been measured and plotted so as to establish a pattern of such intensities and of the circular dichroism relative to the particular specimen (14) under analysis. Such a pattern can be compared (preferably by computer) against known "signature curves" of polarization transmittance of known substances at known concentrations to make possible the identification of substance(s) in the test specimen (14).

It should be readily apparent that certain elements of the preferred embodiment as illustrated in FIG. 1, such as the optical filters, BK-7 lenses (16 and 22) and the Tech 2438 oscilloscope, are not essential components of Applicant's invention, but merely provide greater efficiency in focusing the light and in gathering and analyzing information.

Figure 4A:
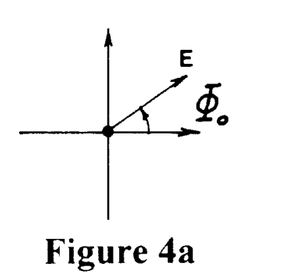
FIGS. 4a–b and 5a–b are graphic representations of the rotation of plane polarized light.
Figure 4B:
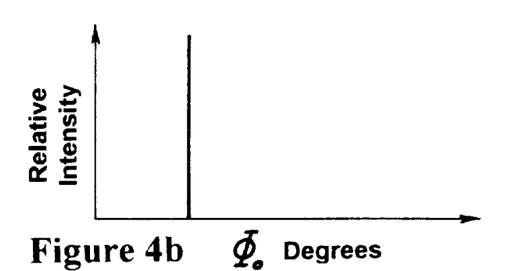
Figure 5A:
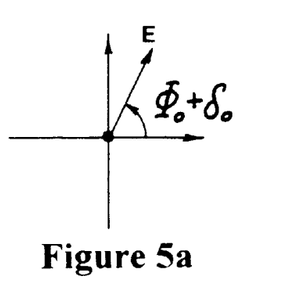
Figure 5B:
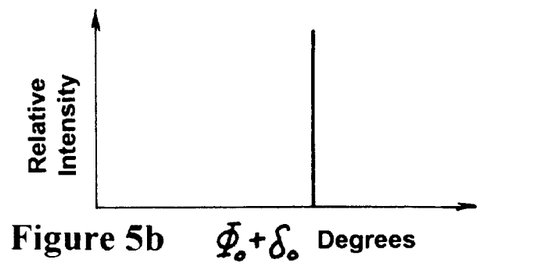
Figure 6A:
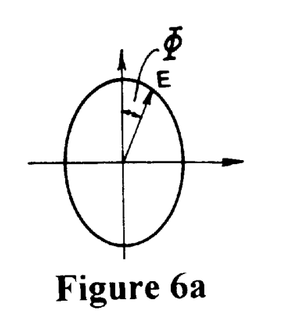
FIGS. 6a–b and 7a–b are graphic representations of circular dichroism of pure elliptically polarized light.
Figure 6B:
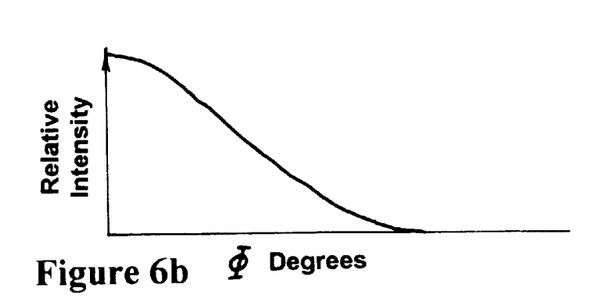
Figure 7A:
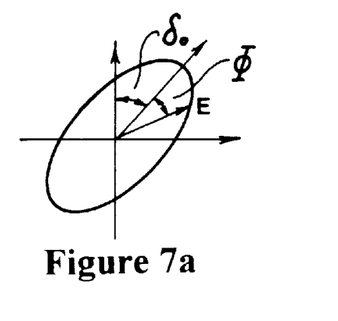
Figure 7B:
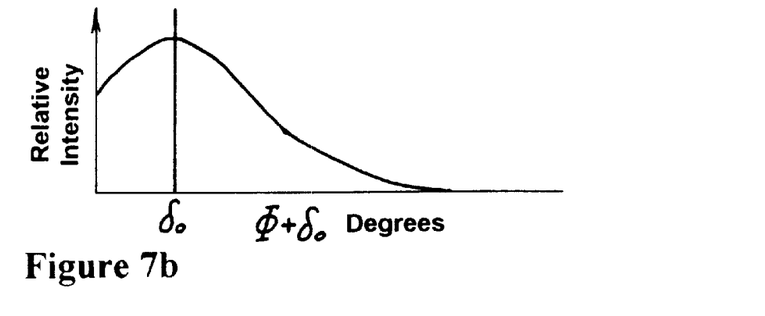
Figure 8A:
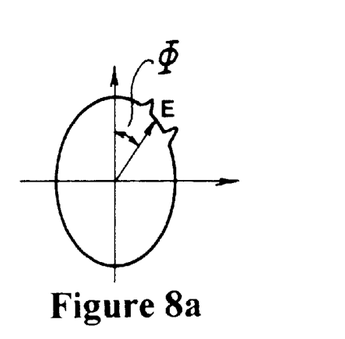
FIGS. 8a–b and 9a–b are graphic representations of circular dichroism of partially polarized light.
Figure 8B:
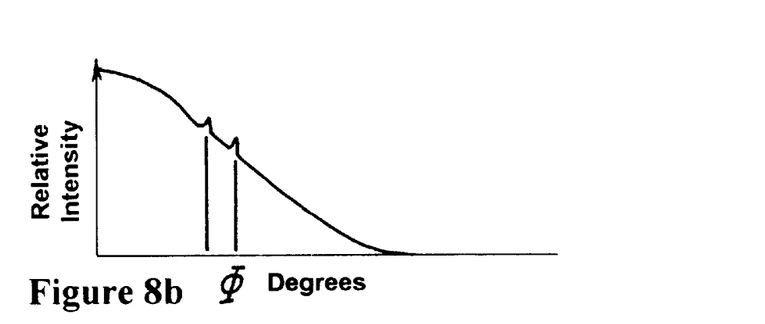
Figure 9A:
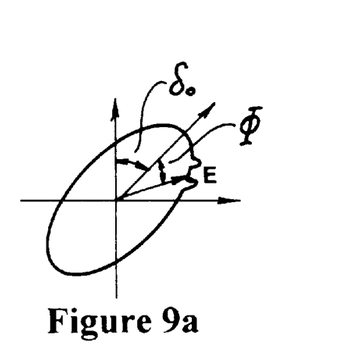
Figure 9B:
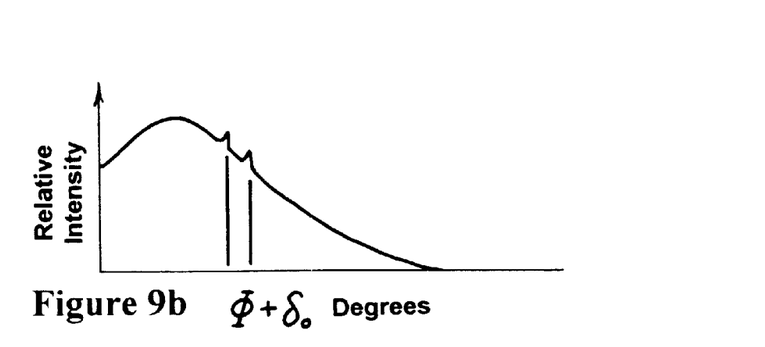
Figure 10:
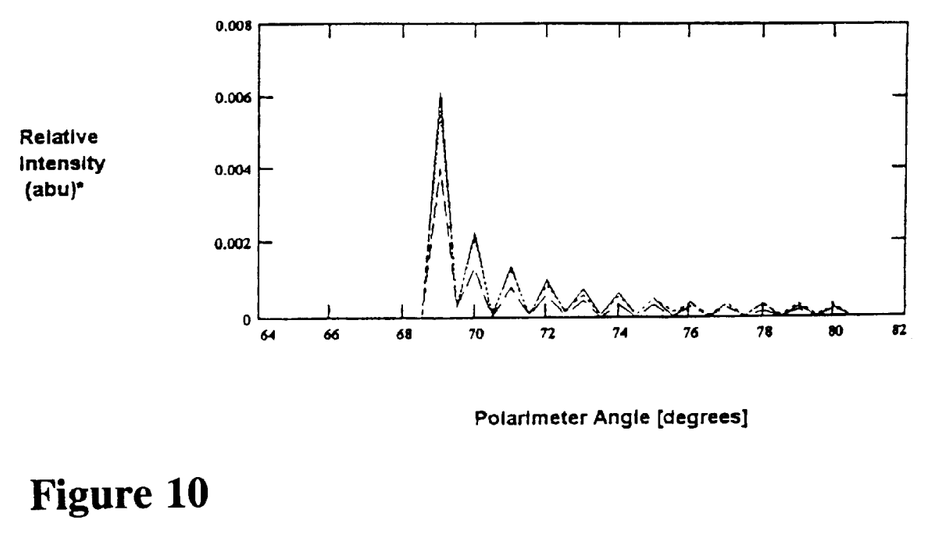
FIG. 10 is the graphical signature of data produced through analysis of a specimen using Applicants' method and apparatus.

Previous measurements that have relied only upon linearly polarized monochromatic light, which yield a single rotational angle, have had difficulty indicating the quantitative presence of a particular substance or molecule in the host material or solution. The apparatus of the present invention approaches the problem with partially polarized polychromatic light—chromatic polarization. Each wavelength possesses a dominant polarization character; in general, elliptical. However, due to the nature of the partially polarized light, the envelope of the dominant polarization is inscribed with a series of spike-like peaks (See FIGS. 8a–b and 9a–b). If the intensity of this light is plotted as a function of the polarization angle, there would be a maximum primary peak, plus a series of secondary peaks displaced at various angles relative to the primary peak. These secondary peaks act as markers increasing the sensitivity of the apparatus of the present invention. When the light is transmitted through a chiral medium, the primary peak shifts by an angular displacement (FIGS. 9a–b). However, each secondary peak possesses its own rotational dynamic, and relative to the primary peak the secondary peaks are now displaced at different angles than before the light entered the chiral medium. FIGS. 4a–b/5a–b, 6a–b/7a–b, and 8a–b/9a–b illustrate in a step-by-step fashion the effects of optical rotary power, circular dichroism, and partial polarization. The subscript naught on the angles in these figures indicates they are fixed. The circular dichroism distorts the shape of the ellipse and thus changes the eccentricity.

Figure 2:
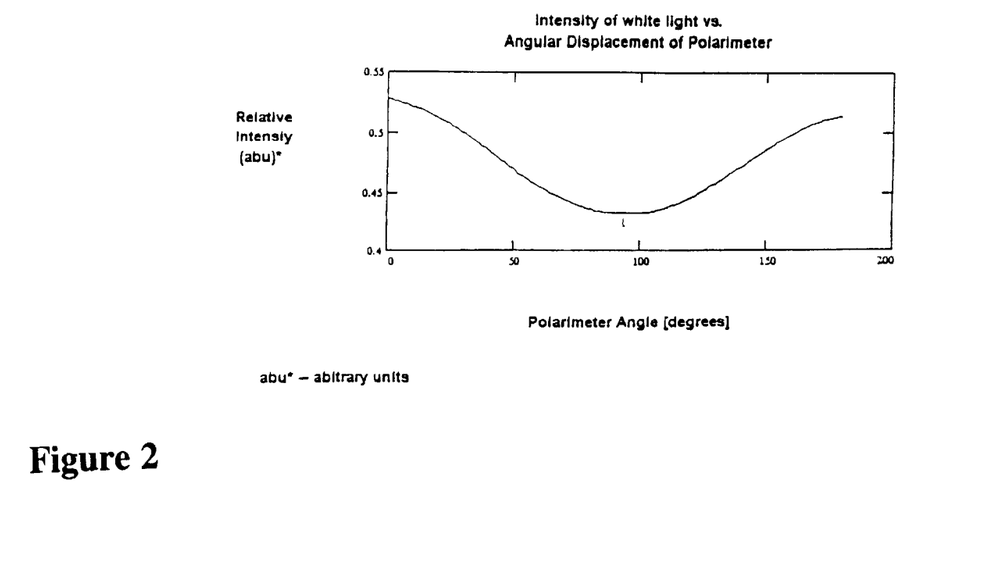
FIG. 2 is a graphic depiction of white light transmission intensity along a continuum of angularly distinguished polarization planes.

FIG. 2 graphically illustrates the distribution of light intensity values (y-axis) of specimen-transmitted white light along a continuum of angularly distinguished polarization planes (x-axis). Such plotting of the polarization plane-specific transmission intensity values at each of a plurality of polarization planes will yield a graphic pattern which is unique for that compound. As demonstrated by FIG. 2, as the planes of polarization at which the light intensity value is measured increase in number, and are plotted, a pattern will exerge, one which can be compared with known patterns for identification purposes.

Figure 3:
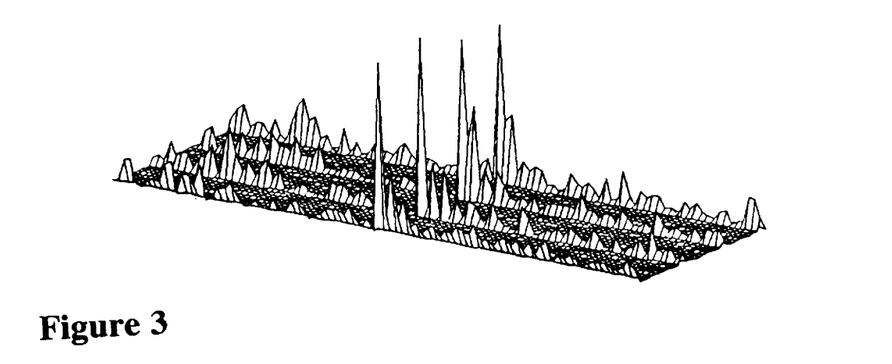
FIG. 3 is a graphic depiction of Fourier-sine transform data of a 10 mg/100 ml solution of dextrose, U.S.P. taken at four distinct wavelengths at 850, 880, 905 and 1065 nanometers.

In addition, as demonstrated by FIG. 3, a different, more detailed pattern is shown in the distribution of light intensity values (y-axis) along a continuum of angularly distinguished polarization planes (x-axis) relative to wavelength-specific bands of light.

Similar patterns based upon the circular dichroism effect of various compounds can be accumulated as shown in FIGS. 6b, 7b, 8b, and 9b. Combining all of these various effects creates a more complex signature but results in a more accurate identification and quantification because more signature data provides a greater ability to distinguish minor variations in the composition of the test specimen.

Use of any or all of these patterns allows identification of a compound in even a complex sample containing multiple compounds. This is true even though certain compounds may exhibit similar polarization patterns at specific wavelengths of light, because no two compounds will exhibit identical transmission patterns at all wavelengths and in all polarization planes, nor do they exhibit the same circular dichroism. Accordingly, even though one component in a sample may "mask" the distribution or characteristics of another component at one or more specific wavelengths, and/or in a few specific polarization planes, there is little chance that this masking effect will effectively skew an analysis involving numerous polarization planes at several specific band widths of light.

It is important to further note that although the gross intensity of light passing through a specimen may vary depending on density of the specimen or the concentration of the compound in the test specimen, the proportional relative values of light transmission intensity at each of numerous polarization planes will remain substantially constant for any given compound. In other words, each birefringent compound yields a "signature curve" of light intensity values at varying polarization planes which curve shifts in toto relative to the y-axis (non-relative, gross light intensity) depending on concentration or density of the sample. This shift of the "signature curve" can, in fact, be used to derive the concentration of a constituent compound once standards for measured compounds are known.

Although the invention has been described with reference to specific embodiments, this description is not meant to be construed in a limited sense. Various modifications of that disclosed embodiments, as well as alternative embodiments of the inventions, will become apparent to persons skilled in the art upon the reference to the description of the invention. It is, therefore, contemplated that the appended claims will cover such modifications that fall within the scope of the invention.

We claim:

1. A device for spectral polarimetric analysis of a test specimen, comprising:

irradiating means for irradiating a test specimen with partially polarized, spectral primary radiation, said irradiating means being placed at a first position;

first polarizing means located at a second position spatially separated from said first position, and oriented for receiving, as a specimen-polarized/specimen-transmitted first radiation subset, that portion of said primary radiation as is transmitted and polarized by said test specimen, and for selectively transmitting, as a second radiation subset of said primary radiation, that portion of said specimen-polarized/specimen-transmitted first radiation subset as resides in a plurality of first polarizing means primary polarization planes; and first radiation intensity measuring means operably positioned relative to said first polarizing means for receiving and measuring the radiation intensity of said second radiation subset at each of a plurality of wave-lengths for each of said plurality of said first polarizing means primary polarization planes.

2. The device of claim 1, wherein said first polarizing means is user adjustable between said first polarizing means primary polarization planes to first polarizing means secondary polarization planes, said first polarizing means secondary polarization planes being angularly distinct from said first polarizing means primary polarization planes.

3. A method for performing a spectral polarimetric analysis of a specimen, comprising the steps of:

selecting a test specimen to be analyzed;

selecting a device, comprising:

irradiating means for irradiating a test specimen with partially polarized, spectral primary radiation, said irradiating means being placed at a first position;

first polarizing means located at a second position spatially separated from said first position, and oriented for receiving, as a specimen-polarized/specimen-transmitted first radiation subset, that portion of said primary radiation as is transmitted and polarized by said test specimen, and for selectively transmitting, as a second radiation subset of said primary radiation, that portion of said specimen-polarized/specimen-transmitted first radiation subset as resides in each of a plurality of first polarizing means primary polarization planes; and first radiation intensity measuring means operably positioned relative to said first polarizing means for receiving and measuring the radiation intensity of said second radiation subset in each of said first polarizing means primary polarization planes;

operably placing said test specimen in the path of irradiation of said irradiating means;

energizing said irradiating means, causing said irradiating means to emit said partially polarized primary radiation; and measuring the intensity of said second radiation subset at each of a plurality of wavelengths for each of said first polarizing means primary polarization planes.

4. The method of claim 3, wherein said first polarizing means is user adjustable between said first polarizing means primary polarization planes to first polarizing means secondary polarization planes, said first polarizing means secondary polarization planes being angularly distinct from said first polarizing means primary polarization planes.

5. The method of claim 4 further comprising the step of measuring the intensity of said second radiation subset in each of said first polarizing means secondary polarization planes.

6. A device for spectroscopic analysis of a test specimen, comprising:

irradiating means for irradiating a spectroscopic test specimen with partially polarized primary radiation, said irradiating means being placed at a first position;

first polarizing means located at a second position spatially separated from said first position, and oriented for receiving, as a specimen-polarized/specimen-transmitted first radiation subset, that portion of said primary radiation as is transmitted and polarized by said spectroscopic test specimen, and for selectively transmitting, as a second radiation subset of said primary radiation, that portion of said specimen-polarized/specimen-transmitted first radiation subset as resides in one or more first polarizing means primary polarization planes; and first radiation intensity measuring means operably positioned relative to said first polarizing means for receiving and measuring the radiation intensity of said second radiation subset in each of said first polarizing means primary polarization planes.

* * * * *